US005606412A

United States Patent [19]
Saito et al.

[11] Patent Number: 5,606,412
[45] Date of Patent: Feb. 25, 1997

[54] FLOW CELL ASSEMBLY

[75] Inventors: Muneo Saito; Hiroyuki Hakozaki; Takeshi Kanomata, all of Hachioji, Japan

[73] Assignee: Jasco Corporation, Hachioji, Japan

[21] Appl. No.: 595,466

[22] Filed: Feb. 5, 1996

[30] Foreign Application Priority Data

Feb. 7, 1995 [JP] Japan .................................. 7-043469

[51] Int. Cl.$^6$ ................................................ G01N 21/05
[52] U.S. Cl. ........................................ 356/246; 356/440
[58] Field of Search ............................ 356/246, 244, 356/440, 436, 73; 250/576; 422/83, 91, 102, 104

[56] References Cited

U.S. PATENT DOCUMENTS 3,951,607  4/1976  Fraser ..................................... 250/576
5,374,399  12/1994  Tsukamoto et al. ..................... 356/246

*Primary Examiner*—Hoa Q. Pham
*Attorney, Agent, or Firm*—Ronald R. Snider

[57] ABSTRACT

A flow cell (112) used for detecting a characteristic of a continuously-flowing fluid comprises a narrow inlet path (118) for the fluid, a flow cell portion (112) having a diameter larger than that of the narrow inlet path (118), and flow-regulating portion (122) which is disposed between the narrow inlet path (118) and the flow cell portion (112) and has a diameter substantially the same as that of the flow cell portion (112) and a plurality of holes (134a to 134d), such that the fluid is introduced from the narrow inlet path (118) into the flow cell portion (112) by way of each of the holes (134a to 134d) of the flow-regulating portion (122).

7 Claims, 12 Drawing Sheets

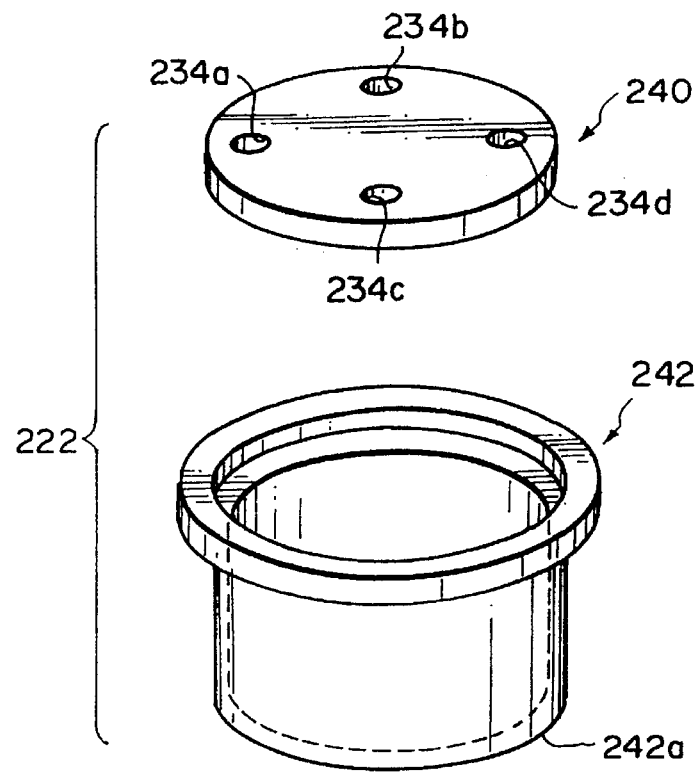
F I G . 7
【図8】
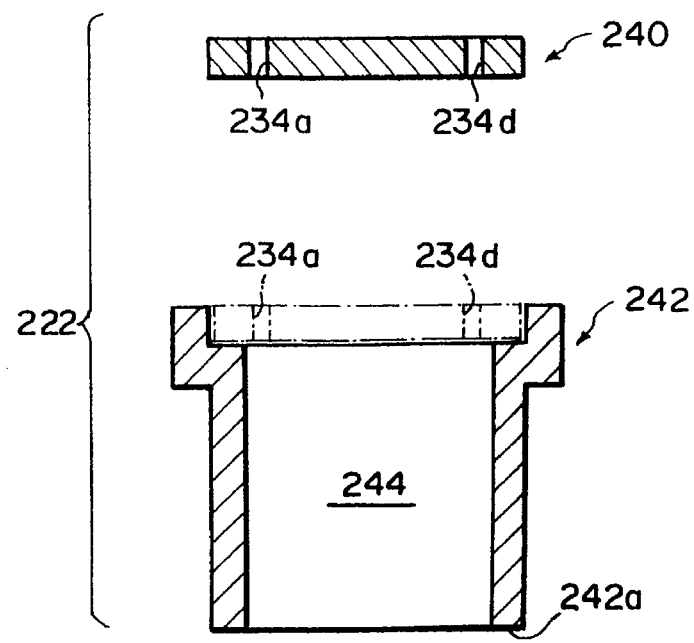
F I G . 8

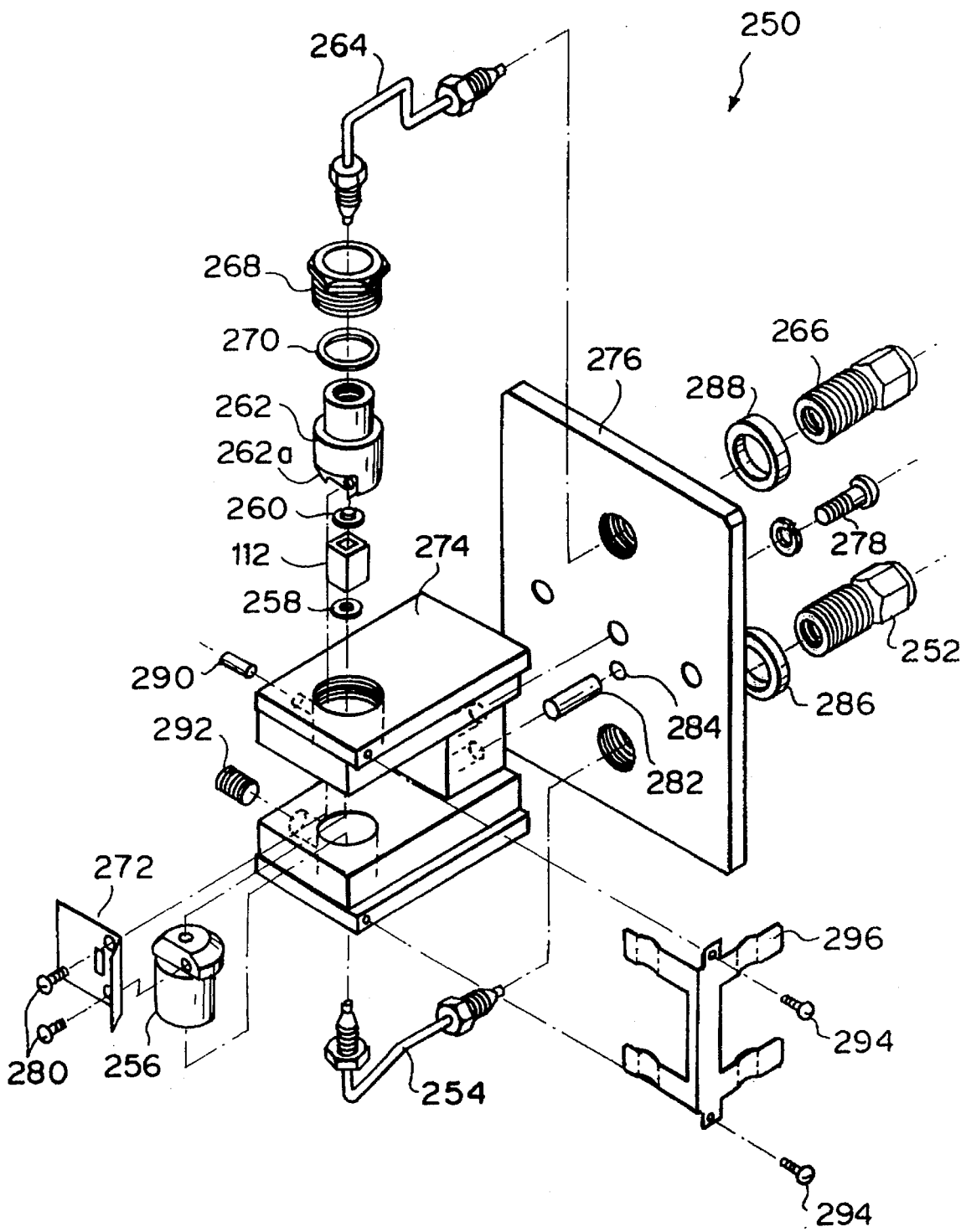
F I G . 1 1

FLOW CELL ASSEMBLY

[FIELD OF THE INVENTION]

The present invention relates to a flow cell assembly and, in particular, to improvement in its mechanism for introducing fluids.

[BACKGROUND OF THE INVENTION]

For example, a fluid to be measured continuously flows from a liquid chromatograph and is introduced into a flow cell such that a characteristic of the fluid is inspected by a desirable detector.

FIG. 1 shows an example of such a flow cell.

In this drawing, a flow liquid 10 from a liquid chromatograph is introduced into a rectangular flow cell 12, which is made of quartz glass, from therebelow. Then, excitation light L1 from a light source 14 is made incident on one side surface 12a of the flow cell 12. When the flow liquid 10 to be measured within the flow cell 12 emits fluorescence, fluorescence L2 obtained in a direction orthogonal to the excitation light L1 is detected by a detector 16.

Thus configured flow cell 12 can continuously measure the fluorescent materials existing in the flow liquid 10 flowing from the liquid chromatograph.

Here, a tube having a bore of not greater than 0.25 mm is usually used for connecting a column and a flow cell to each other in order to prevent the sample separated in the column from diffusing within the tube. Accordingly, at a usual liquid supply flow rate of 0.5 to 3.0 ml/min, the average flow velocity within the tube becomes 17 to 100 cm/sec, which is very fast.

As the quartz cell used as a flow cell, one having a capacity of 10 to 50 μl is used as a standard cell for a liquid chromatograph. Based on this capacity, the flow cell has a size within the range of about 1.5×1.5 (defining the size of a plane perpendicular to the flow direction)×5.0 mm (defining the size in the flow direction) to 3.0×3.0×5.0 mm. Though the sensitivity of the detector increases as the capacity of the flow cell is larger, two components, for example, which are sufficiently separated from each other by a column may mix within the flow cell, thereby making it difficult for a chromatogram, which records the signal output from the detector, to sufficiently separate these two components from each other and thus deteriorating the accuracy in quantitative analysis. Therefore, the capacity of the flow cell should be restricted to the above-mentioned range.

As explained above, since the diameter of the tube connecting the column and the flow cell to each other and that of the flow cell greatly differ from each other, the flow cell and the tube have conventionally been connected to each other as shown in FIG. 2.

In FIG. 2, the flow cell 12 and a tube 18 is connected to each other by a flow-cell holding portion 20 and an inlet gasket 22. As shown in this drawing, an opening 20a is formed at the center of the flow-cell holding portion 20 so as to receive the tube 18, whereas the upper portion of the opening 20a is this drawing has an opening 20b having a slightly larger diameter into which the inlet gasket 22 is fitted. The tube 18 and inlet gasket 22 positioned by these openings 20a and 20b are fixed such that their conduits 18a and 22a communicate with each other.

On the other hand, the flow cell 12 is tightly fixed such that its lower opening 12b is pressed against the inlet gasket 22.

When a buffer solution is used as a mobile phase for a high-performance liquid chromatograph (HPLC), a salt in the buffer solution may be deposited on the inner surface of the tube connecting the column and the flow cell to each other, thereby blocking the tube or, when a fruid to be measured is supplied to thus blocked tubing from the flow cell portion, the flow cell may be broken. Also, when the apparatus is not used for a long time, mold or the like may be generated, thereby blocking the tube or breaking the flow cell as well.

When the tube is blocked, since it is relatively easy to obtain a new tube, not a skilled maintenance engineer but a user usually exchanges thus blocked tube for a new one. Also, when the flow cell is broken, not a skilled maintenance engineer but a user usually exchanges thus broken flow cell for a new one.

However, there has been a problem that the peak resolution remarkably decreases when the tube or flow cell is exchanged.

In order to investigate the cause of this problem, the inventors have conducted the following tests.

Namely, the following Table 1 (A, B group) shows the results of comparison of the case in which a special tool is used for adjusting the position where the flow cell is attached with the case in which the position where the flow cell is attached is adjusted by visual observation without using the special tool. Also, this table (C, D group) shows the results of comparison of the case in which burrs formed upon processing of the inlet end surface of the tube are sufficiently removed with the case in which they are not sufficiently removed.

In this analysis system, in order to verify the diffusion within the cell, acetonitrile as a mobile phase, 0.1% benzene as a sample, and a reversed-phase column are used so as to generate a condition under which the sample is not retained within the column.
(Compared Items)

A: Case in which a special tool is used for adjusting the position where the flow cell is attached.

B: Case in which, without using a special tool, the position where the flow cell is attached is adjusted by visual observation.

C: Case in which burrs formed upon processing of the inlet end surface of the tube are sufficiently removed.

D: Case in which burrs formed upon processing of the inlet end surface of the tube are not sufficiently removed.
(Method of Evaluation)

In this analysis system, the number of theoretical plates (NTP) of benzene peak is used as an index for evaluation, which is represented by the following equations (1) and (2):

$$NTP = (t_R/\sigma)^2 \quad (1)$$

$$\sigma = A/\sqrt{(2\pi * H)} \quad (2)$$

wherein $T_R$ is retention time of benzene peak, A is area value of benzene peak, and H is height value of benzene peak.

TABLE 1

| Compared Item | Conventional Flow Cell |
| --- | --- |
| A group | 5,600 |
| B group | 4,100 |
| C group | 5,450 |
| D group | 3,950 |

For example, in FIG. 3, in order to exchange the tube 18 for a new one, an inlet end surface 18c having a bore of not greater than 0.25 mm has to be processed. The user who is not skilled in such processing cannot sufficiently remove the burrs formed upon the processing of the inlet end surface 18c and thus cannot uniformly process the flow path surface shape of the tube 18. Accordingly, as shown in Table 1, the processing accuracy at the inlet end surface 18c of the tube 18 cannot be controlled. When the flow path surface is not uniformly shaped, the flow rate distribution of the fluid running through the flow cell 12 may be disturbed.

Also, it is very difficult even for a skilled engineer to sufficiently remove the burrs formed when the inlet end surface 18c of the tube 18 having a bore of not greater than 0.25 mm is processed. When the processing accuracy of the inlet end surface 18c is increased to an extent where the flow rate distribution of the fluid running through the flow cell 12 is not disturbed, its manufacturing cost may increase, thereby making it impossible to reduce the cost.

Further, as mentioned above, the flow cell has a size within the range of about 1.5×1.5 (defining the size of a plane perpendicular to the flow direction)×50 mm (defining the size in the flow direction) to 3.0×3.0×5.0 mm and is very small. Accordingly, in order to exchange the flow cells, the position where the flow cell is attached has to be adjusted within the range of 1 mm or less. Such an adjustment is very difficult for a user who has neither special tool nor skill. As shown in Table 1 (A, B Group), when the position where the flow cell is attached is not adjusted appropriately, the flow rate distribution of the fluid running through the flow cell may be disturbed as well.

Thus, when the user performs maintenance of the apparatus, the flow rate distribution of the fluid running through the flow cell may be disturbed in any case. Then, when the flow rate distribution of the fluid running through the flow cell is deteriorated, the two components which have been sufficiently separated from each other by the column may mix within the flow cell as mentioned above, thereby making it difficult for a chromatogram, which records the signal output from the detector, to sufficiently separate these two components from each other and thus deteriorating the accuracy in quantitative analysis.

In order to overcome these problems, a skilled maintenance engineer may be asked to make repairs. However, as compared with the case where the user performs maintenance, it takes days for the skilled engineer to come while necessitating labor cost to be paid therefor. Accordingly, it is not a preferable means for overcoming the problems.

[SUMMARY OF THE INVENTION]

In view of the foregoing problems of the prior art, the object of the present invention is to provide an exchangeable flow cell assembly which can reduce generation of scattered light, while enabling analysis of a fluid without damaging the peak resolution, when not a skilled maintenance engineer but a user exchanges a clogged tube or broken flow cell.

In order to attain this object, the low cell assembly in accordance with the present invention comprises a narrow inlet path for a fluid, a flow cell portion having a diameter larger than that of the narrow inlet path, a flow-regulating portion which is disposed between the narrow inlet path and the flow cell portion and has a diameter substantially the same as that of the low cell portion and a plurality of holes, such that a fluid is introduced from the narrow inlet path into the flow cell portion by way of each of the holes of the flow-regulating portion.

Preferably, as the flow cell portion, a rectangular flow cell whose outer and inner wall surfaces are formed like those of a hollow square pole is used, while the flow-regulating portion has at least four holes respectively at portions corresponding to four corners of the rectangular flow cell.

Preferably, the fluid to be tested is introduced from below the rectangular flow cell, while incident light enters the rectangular flow cell from one surface thereof and the fluorescence emitted from a surface neighboring the surface of incidence is detected.

Preferably, the flow cell portion has a flow-cell holding portion which is attached to the lower opening of the flow cell portion by pressure fit, while the flow-cell holding portion comprises a first opening formed at a center portion thereof into which the narrow inlet path is detachably inserted and a second opening formed on a side of the first opening facing the flow cell portion into which the flow-regulating portion is fitted, such that the flow cell portion and the narrow inlet path are exchangeable.

Preferably, assuming that the size of the plane perpendicular to the flow direction is a×a, the rectangular flow cell is configured so as to satisfy the conditional expression of a >3.0 mm.

Preferably, the clearance between the narrow inlet path opening and the flow-regulating portion is not greater than 2 mm.

Since the flow cell in accordance with the present invention has the flow-regulating portion as mentioned above, the fluid flowing from the narrow inlet path is introduced into the flow cell portion by way of the flow-regulating portion through its plurality of holes.

As the fluid from the narrow inlet path is introduced into the flow cell portion by way of the flow-regulating portion, the fluid can appropriately flow even when, upon exchange of the flow cell portion or narrow inlet path, the position where the flow cell portion is attached has not been appropriately adjusted or the burrs formed at the inlet end surface of the narrow inlet path have not sufficiently been removed.

When a rectangular flow cell whose outer and inner wall surfaces are formed like those of a hollow square pole is used as a flow cell portion, the reflection of the excitation light incident on the flow cell portion can be directed to a predetermined direction, thereby reducing the generating of scattered light. Also, when at least four holes are respectively disposed at portions corresponding to four corners of the rectangular flow cell, the fluid can appropriately flow through the flow cell, thereby greatly improving the peak resolution.

Also, when the flow cell portion has a flow-cell holding portion which is attached to the lower opening of the flow cell portion by pressure fit, while the flow-cell holding portion comprises a first opening formed at a center portion thereof into which the narrow inlet path is detachably inserted and a second opening formed on a side of the first opening facing the flow cell portion into which the flow-regulating portion is fitted, each of the flow cell portion and the narrow inlet path becomes exchangeable.

[BRIEF DESCRIPTION OF THE DRAWINGS]

FIG. 7 is a perspective view showing an inlet gasket which is characteristic to the second embodiment of the present invention;

FIG. 8 is an exploded cross-sectional view showing an inlet gasket which is characteristic to the second embodiment of the present invention;

FIG. 11 is an explanatory view showing a specific state in which the flow cell assembly in accordance with this embodiment of the present invention is used;

[DETAILED DESCRIPTION OF THE PREFERRED EMBODIMENTS]

In the following, embodiments of the present invention will be explained with reference to the drawings.

Figure 1:
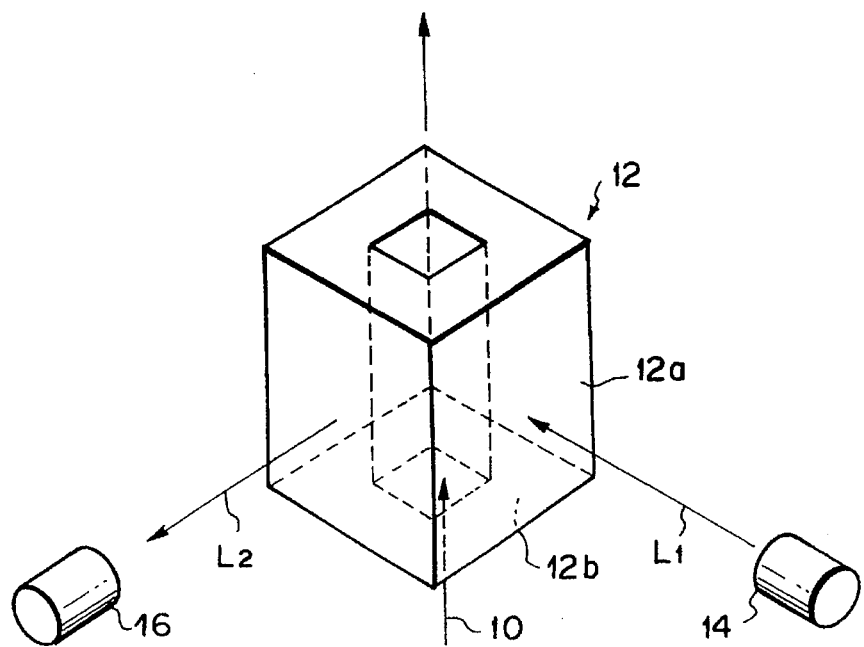
FIG. 1 is an explanatory view showing a schematic configuration of a typical conventional flow cell used for measuring fluorescence.
Figure 2:
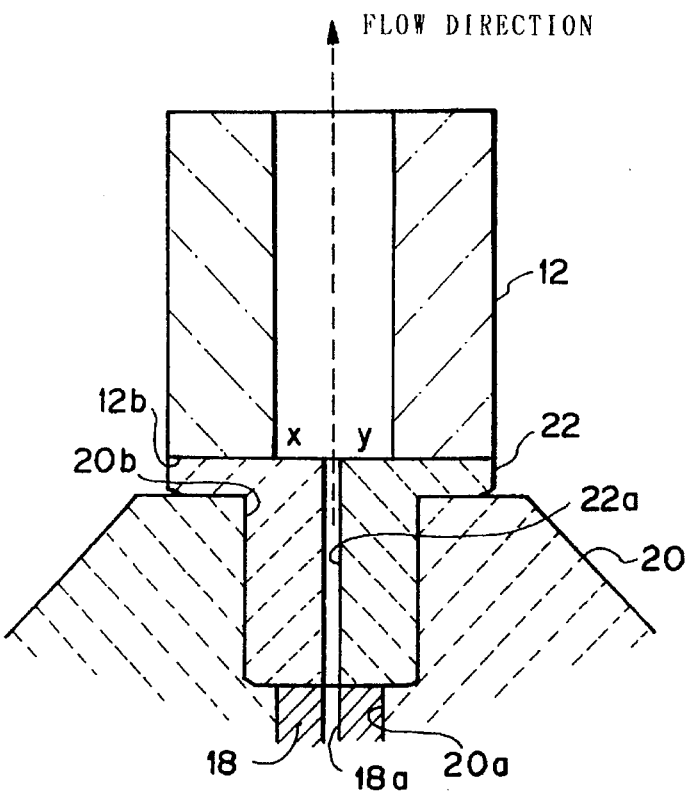
FIG. 2 is an explanatory view showing a state in which the conventional flow cell and a tube are connected to each other.
Figure 3:
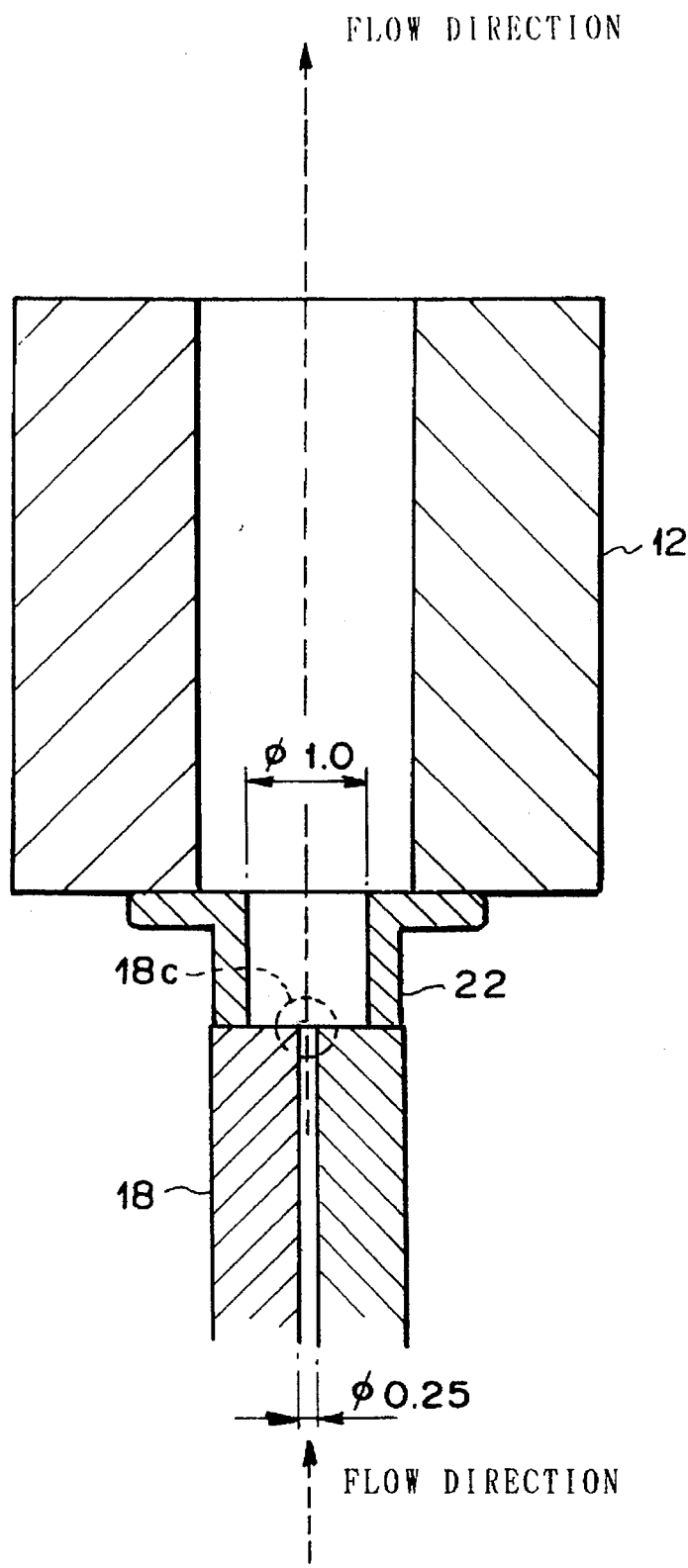
FIG. 3 is an explanatory view showing the problems of the conventional flow cell.
Figure 4:
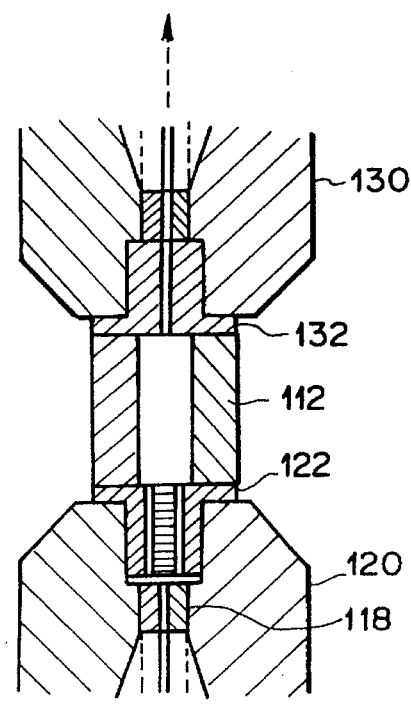
FIG. 4 is an explanatory view showing an overall configuration of the flow cell assembly in accordance with the first embodiment of the present invention.

FIG. 4 shows a schematic configuration of the flow cell in accordance with the first embodiment of the present invention. In this drawing, parts corresponding to those of FIG. 2 are referred to with numerals in which 100 is added to those of FIG. 2, without repeating their explanations.

In FIG. 4, a low cell portion 112 is held between a lower flow-cell holding portion 120 and an upper flow-cell holding portion 130 by way of an inlet gasket 122 and an outlet member 132.

Figure 5:
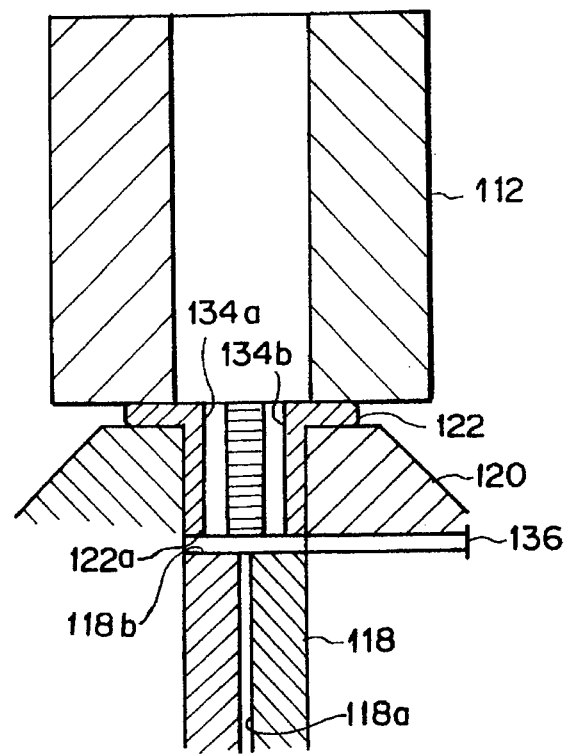
FIG. 5 is an explanatory view showing a state in which the flow cell in accordance with the first embodiment of the present invention and a tube are connected to each other.
Figure 6:
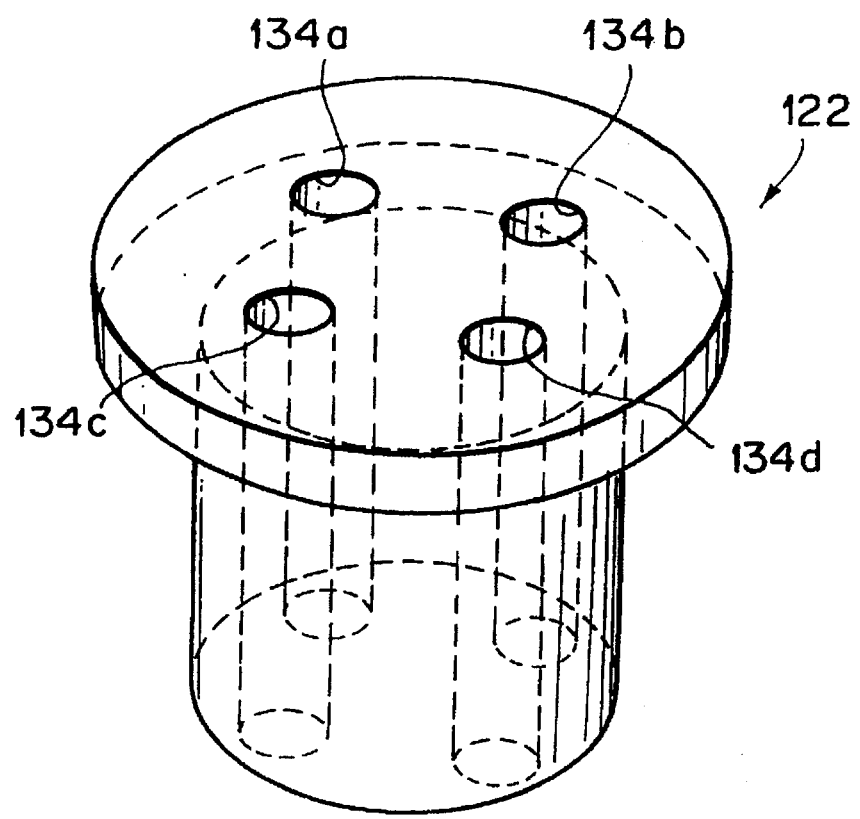
FIG. 6 is an explanatory view showing an inlet gasket which is characteristic to the fist embodiment of the present invention.

FIG. 5 shows the connecting portion between the flow cell portion 112 and a tube (narrow inlet path) 118, whereas FIG. 6 shows the inlet gasket (flow-regulating portion) 122 which is characteristic to this embodiment. The flow-regulating portion 122 has a diameter which is substantially the same as that of the flow cell 112.

As shown in these drawings, the inlet gasket 122 in this embodiment has a plurality of holes 134a, 134b, 134c, and 134d which are disposed away from its center portion. Between a bottom surface 122a of the inlet gasket 122 and a tip surface 118b of the tube 118, a clearance 136 of about 0.5 mm is formed.

When this clearance 136 exceeds 2 mm, a liquid may unfavorably be retained at the clearance 136.

The flow cell in accordance with the present invention is substantially configured as explained in the foregoing. In the following, operations thereof will be explained.

First, when a fluid to be measured supplied by way of the tube 118 reaches the clearance 136, it is ejected from the tip of the tube 118 with a high speed. However, since it collides with the bottom surface of the inlet gasket 122, it does not proceed into the flow cell portion 112 at the high speed. Namely, after filling the clearance 136, it proceeds into the flow cell portion 112 from corner portions in the bottom surface of the rectangular flow cell portion 112 by way of the plurality of holes 134a to 134d.

Accordingly, the flow rates from the respective holes to the flow cell portion 112 become higher at portions corresponding to its four corners, thereby preventing fluid-retaining portions from occurring. Therefore, the fluid-retaining portions can be remarkably reduced, thereby maintaining the resolution at a high level.

Also, even when the positional relationship between the tube 118 and the flow cell portion 112 is shifted or turbulence occurs in the flow from the tube, such a disturbance can be adjusted by the inlet gasket 122. Accordingly, the influence thereof is quite small.

FIGS. 7 and 8 show the second embodiment of the present invention. In this embodiment, parts corresponding to those of the first embodiment are referred to with numerals in which 100 is added to those of the first embodiment, without repeating their explanations.

FIG. 7 is a perspective view showing an inlet gasket 222 which is characteristic to the second embodiment, whereas FIG. 8 is a cross-sectional view thereof.

In this embodiment, the inlet gasket 222 constituting a flow-regulating portion comprises a flow-regulating plate 240 and a cylindrical body 242 having an upper portion into which the flow-regulating plate 240 can fit.

In the state where flow-regulating plate 240 is fitted into the upper portion of the cylindrical body 242, a lower end 242a of the cylindrical body is brought into contact with the upper end of the tube. In this embodiment, even when a clearance such as that in the first embodiment is not provided between the inlet gasket and the tube, the flow liquid can be diffused into respective holes 234a to 234d by way of an internal space 244 within the cylindrical body 242, thereby attaining the effects similar to those of the first embodiment.

While four holes are formed in each of the foregoing embodiments, without being restricted thereto, the effects of the present invention can be obtained when at least two holes are provided.

Figure 9:
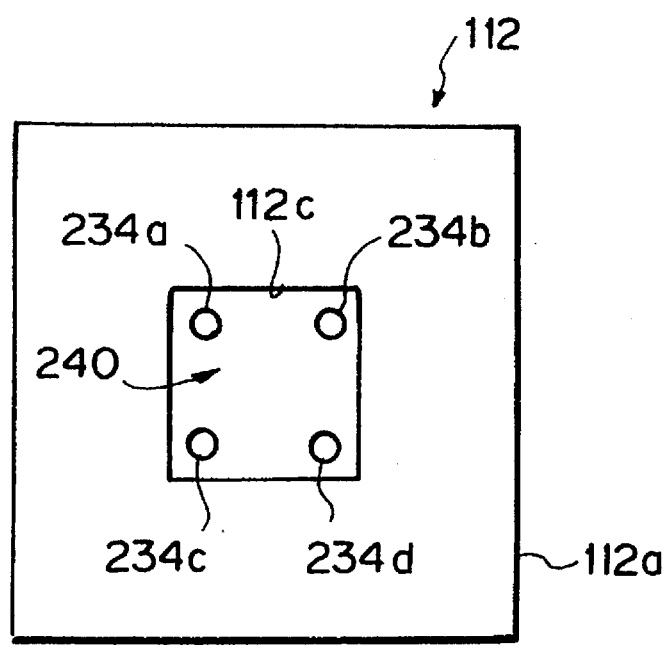
FIG. 9 is an explanatory view showing positions of holes which are characteristic to the flow cell in accordance with the present invention.

However, when holes are applied to the rectangular flow cell portion 112 as in the case of the first embodiment, it is preferable that at least four holes 234 a, 234b, 234c, and 234d are disposed at portions corresponding to the four corners of the flow cell portion 112 as shown in FIG. 9. This drawing is a plan view showing the rectangular flow cell portion 112 viewed from thereabove.

As can be seen from this drawing, when the rectangular flow cell portion 112 whose outer wall surface 112a and inner wall surface 112c are formed like those of a hollow square pole is used. The reflection of the excitation light incident on the flow cell portion 112 can be directed to a predetermined direction, thereby reducing the generation of scattered light.

Also, when at least four holes 234a, 234b, 234c, and 234d are disposed at portions corresponding to the four corners of the rectangular flow cell portion 112, the fluid near the wall surfaces including the four corners within the rectangular flow cell portion can appropriately flow as well, thereby greatly improving the peak resolution.

FIGS. 10 to 14 show specific states in which the flow cell assembly in accordance with such an embodiment is used.

Figure 10:
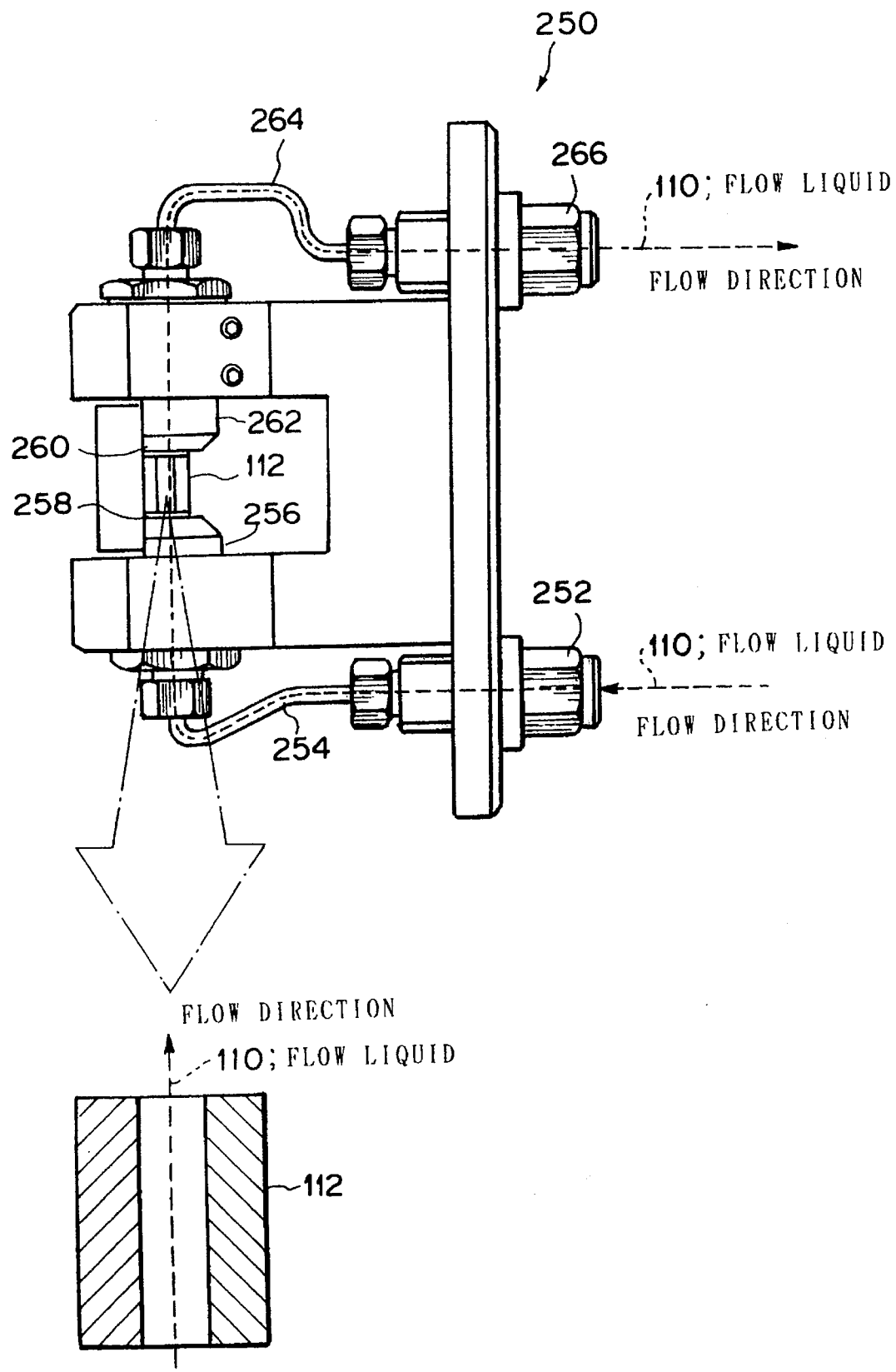
FIG. 10 is an explanatory view showing a specific state in which the flow cell assembly in accordance with an embodiment of the present invention is used.

In a flow cell assembly 250 shown in FIG. 10, a flow liquid 110 from a liquid chromatograph passes through an inlet union 252, an inlet tube 254, an inlet cell holder 256, and an inlet gasket 258 so as to be introduced into the quartz cell 112. The flow liquid passing through the quartz cell 112 is output from an outlet gasket 260 and successively passes through an outlet cell holder 262, an outlet tube 264, and an outlet union 266.

FIG. 11 is an exploded perspective view showing the flow cell assembly 250 in accordance with this embodiment.

As shown in this drawing, the flow cell assembly 250 comprises the outlet tube 264, a cell-holding screw 268, a sheet 270, the outlet cell holder 262, the outlet gasket 260, the quartz cell 112, the inlet gasket 258, the inlet cell holder 256, a cell mask 272, the inlet tube 254, a cell body 274, a cell panel 276, a cell-panel fixing screw 278, a mask-fixing screw 280, a pin 282, a hole 284, the inlet union 252, the outlet union 266, an inlet collar 286, a pin 290, a grub screw 292, a screw 294, and a filter holder 296.

The cell-holding screw 268 is disposed such that the inlet cell holder 256 and the outlet cell holder 262 securely hold the quartz cell 112 therebetween, whereby a sufficient resistance to pressure can be obtained.

Between the cell-holding screw 268 and the outlet cell holder 262, a spacer having a favorable sliding characteristic is disposed as the sheet 270.

The cell-holding screw 268 and the cell body 274 respectively have a thread and a groove such that the cell-holding screw 268 can engage with this groove. Also, in order to prevent the outlet cell holder 262 from rotating when the cell-holding screw 268 engages with the cell body 274, a groove 262a is provided with the outlet cell holder 262. Since the pin 290 is disposed in the groove 262a of the outlet cell holder 262 so as to proceed from a side of the cell body 274, the outlet cell holder 262 is prevented from rotating with respect to the cell body 274.

The outlet cell holder 262 has a guide groove which corresponds to the size of the quartz cell 112 used. Accordingly, even when the quartz cell 112 is exchanged for a new one, the latter can easily be attached to a predetermined position as long as it has the same shape.

While the cell mask 272 functions as a slit for the fluorescence emitted from the quartz cell, it can also prevent the stray light formed by the excitation light irregularly reflected by the surface of the quartz cell 112 from entering a detector, for example.

Figure 12:
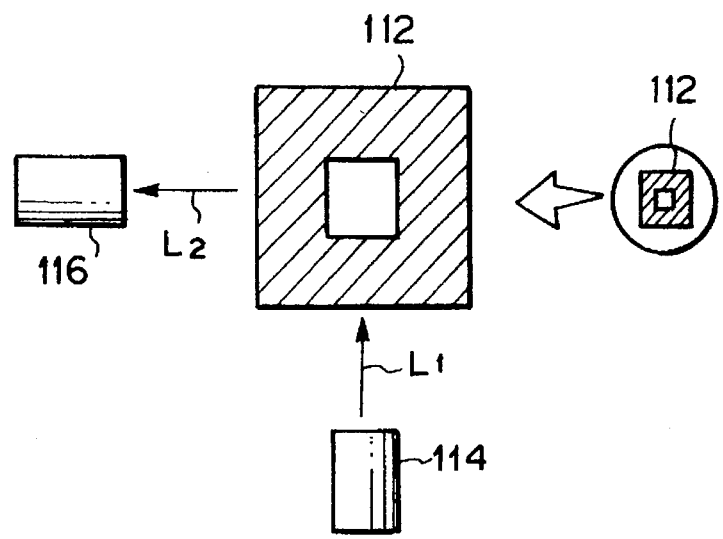
FIG. 12 is an explanatory view showing a specific state in which the flow cell assembly in accordance with this embodiment of the present invention is used.

FIG. 12 is a plan view showing the flow cell in accordance with this embodiment viewed from thereabove.

As shown in this drawing, excitation light L1 is made incident on one side surface of the flow cell 112. When the flow liquid to be measured within the flow cell 112 emits fluorescence, fluorescence L2 obtained in a direction orthogonal to the excitation light L1 is detected by a detector 116.

In this manner, when an optical disposition is arranged such that the excitation light L1 is emitted from a direction orthogonal to a direction for observing the fluorescence L2, the reflected light from the cell 112 or the like, which may result in stray light, can be prevented from entering a measurement system (e.g., detector 116).

Figure 13:
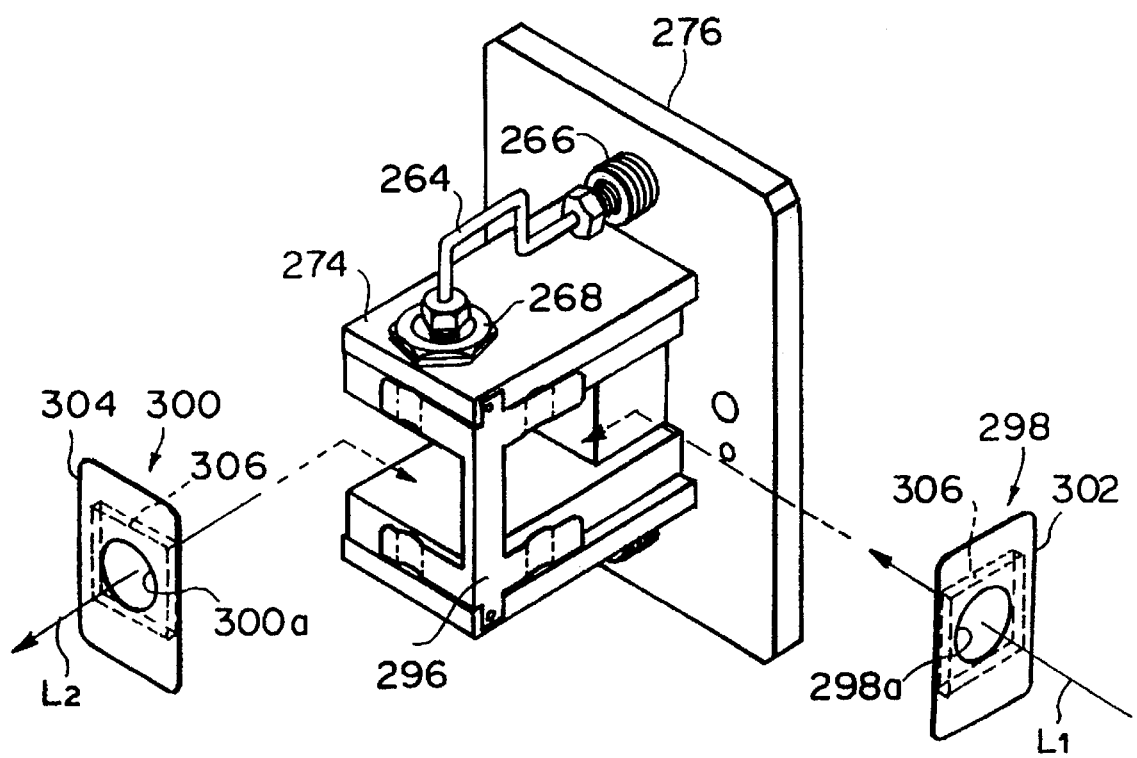
FIG. 13 is an explanatory view showing a specific state in which the flow cell assembly in accordance with this embodiment of the present invention is used.

As shown in FIG. 13, transmission filters 298 and 300 may be respectively formed by substrates 302 and 304 having substantially circular holes 302a and 304a, which are disposed on the courses where the excitation light L1 and the fluorescence L2 pass through, and filters 306 such as color glass filter or interference filter fixed thereto.

In this drawing, the transmission filter 298 can be disposed between the cell body 274 and the filter holder 296 so as to be detachable from the upper right portion in the drawing. The transmission filter 300 can be disposed between the cell body 274 and the filter holder 296 so as to be detachable from the upper left portion in the drawing.

Since the transmission filters 298 and 300 can be detachably disposed with respect to the cell body 274 and the filter holder 296, transmission filters having various performances can be easily exchanged therefor.

Figure 14:
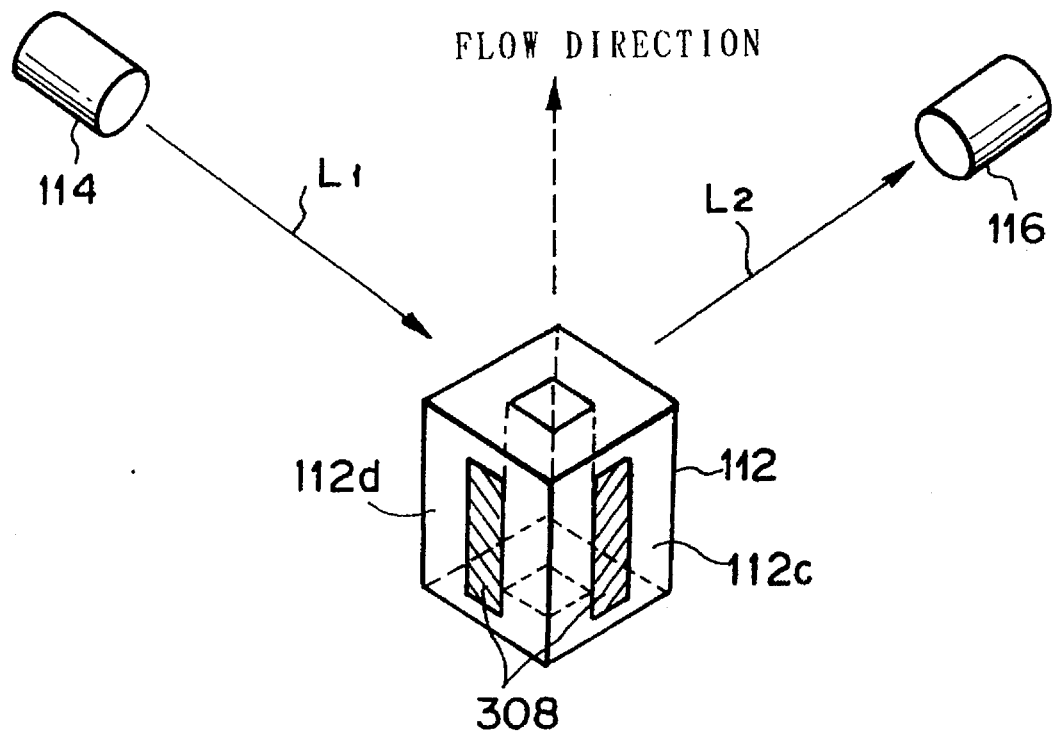
FIG. 14 is an explanatory view showing a flow cell portion which is characteristic to this embodiment of the present invention.

As shown in FIG. 14, in the quartz cell 112, an outer surface 112c of a window plate opposite a window plate on which the excitation light L1 is incident is coated with a thin layer of aluminum 308. Similarly, an outer surface 112d of a window plate opposite a window plate from which the fluorescence L2 is emitted is coated with a thin layer of aluminum 308.

When the outer surface 112c of a window plate opposite a window plate on which the excitation light L1 is incident and the outer surface 112d of a window plate opposite a window plate from which the fluorescence L2 is emitted are respectively coated with thin layers of aluminum 308 in this manner such that the excitation light L1 is reflected by the wall surface 112c, the flow fluid 110 can be efficiently irradiated with the excitation light L1. Also, since the fluorescence L2 is reflected by the wall surface 112d, it can efficiently enter the detector 116.

As a result, the light quantity of the fluorescence L2 can be about 2.5 to 3.5 times as high as that obtained without the coating of aluminum 308, whereby characteristic analysis can be performed more sensitively.

As shown in this drawing, not the whole but only a part of the wall surfaces 112c and 112d is coated with a layer of aluminum 308 so that stray light can be transmitted through the wall surfaces 112c and 112d without being reflected thereby, whereby most of the stray light can be decreased, while the fluorescence can be reflected in large quantities.

Also, when a thick layer of silicon dioxide is coated on any layer of aluminum 308, the layer of aluminum 308 can be protected from mechanical and chemical stresses.

Figure 15:
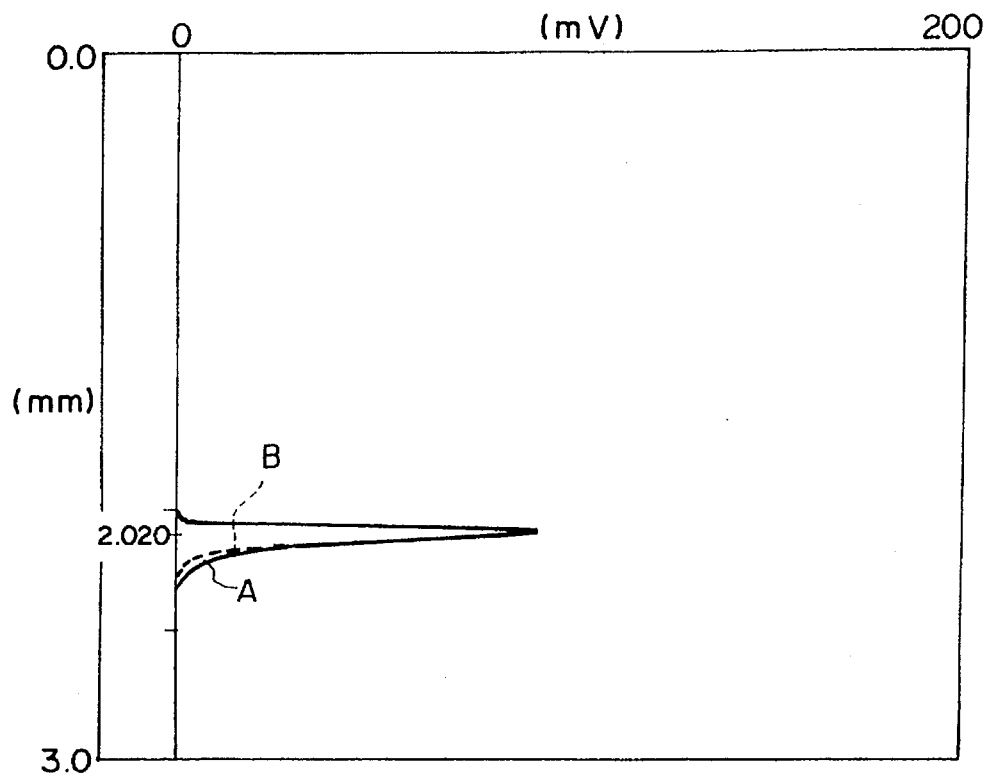
FIG. 15 is a chart comparing the results of detection obtained when special tool is used for adjusting the position where the flow cell in accordance with the present invention is attached with those obtained when the position where the flow cell is attached by visual observation without using the special tool.

FIG. 15 shows the results of comparison of the case in which a special tool is used for adjusting the position where the flow cell in accordance with the present invention is attached with the case in which the position where the flow cell is attached is adjusted by visual observation without using the special tool.

In this analysis system, in order to verify the diffusion within the cell, acetonitrile as a mobile phase, 0.1% benzene as a sample, and an reversed-phase column are used so as to generate a condition under which the sample is not retained.

In this chart, curve A showing the case where no special tool is used and curve B showing the case where the special tool is used have similar peaks and sample-retaining characteristic in the flow cell.

Thus, in the flow cell in accordance with the present invention, even when, upon exchange of the flow cells, the position where the flow cell is attached is adjusted without using a special tool, the retention of the sample within the flow cell can be remarkably reduced as in the case where the special tool is used, whereby the diffusion can be reduced.

Though the foregoing embodiments explain the cases where rectangular cells are used for detecting fluorescence, without being restricted thereto, the present invention may be applied to cells having various shapes such as cylindrical cells used for measuring absorbance.

In the following, a preferable example of the present invention will be explained more in detail. However, the present invention should not be restricted thereto.

EXAMPLE 1

The following Table 2 shows the results of comparison of the case in which the flow cell in accordance with this embodiment is used with the case in which a conventional flow cell having the same shape is used.

In this analysis system, in order to verify the diffusion within the cell, the same conditions are noted above Table 1 was applied.

Also, in this analysis, in order to evaluate an index, the same equations as noted equations (1) and (2) were applied to elevation.
(Compared Items)
A: Case in which a special tool is used for adjusting the position where the flow cell is attached.
B: Case in which, without using a special tool, the position where the flow cell is attached is adjusted by visual observation.
C: Case in which burrs formed upon processing of the inlet end surface of the tube are sufficiently removed.
D: Case in which burrs formed upon processing of the inlet end surface of the tube are not sufficiently removed.

TABLE 2

| Compared Item | Embodiment | Conventional |
| --- | --- | --- |
| A group | 5,950 | 5,600 |
| B group | 5,300 | 4,100 |
| C group | 5,500 | 5,450 |
| D group | 5,650 | 3,950 |

As evidenced by these results, effects are remarkably improved in the cases of the compared items of B and D.

Accordingly, in the flow cell assembly in accordance with the present invention, even when the position where the flow cell is attached cannot be appropriately adjusted as compared with the case where a skilled maintenance engineer is called, for example, when a user with neither skill nor special tool exchanges the flow cell or tube for a new one, or when the inlet end surface of the tube cannot be uniformly processed, the diffusion of the sample within the flow cell can be remarkably reduced as in the case where the skilled engineer exchanges the flow cell or tube for a new one.

Figure 16:
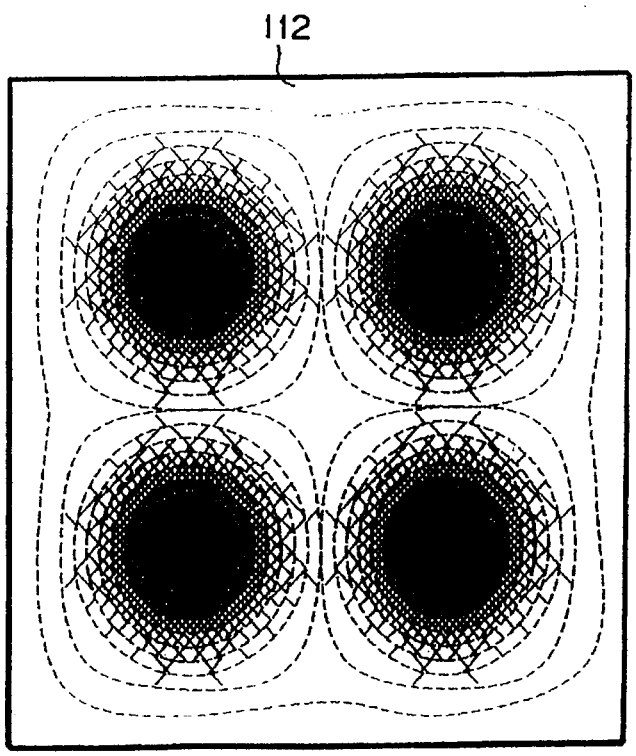
FIG. 16 is an explanatory view showing an operation in this embodiment of the present invention.

Also, as shown in FIG. 5, when a fluid to be measured supplied by way of the tube 118 reaches the clearance 136, it is ejected from the tip of the tube 118 with a high speed. However, since it collides with the bottom surface of the inlet gasket 122, it does not proceeds into the flow cell portion 112 still with the high speed. Namely, after filling the clearance 136, it proceeds into the flow cell portion 112 from corner portions in the bottom surface of the rectangular flow cell portion 112 by way of the plurality of holes 134a to 134d. Accordingly, as shown in FIG. 16, the flow rates from the respective holes into the flow cell 112 become higher at portions where the rate has conventionally tended to be remarkably slowed, thereby preventing the retaining portions such as x and y portions shown in FIG. 2 from occurring.

Figure 17:
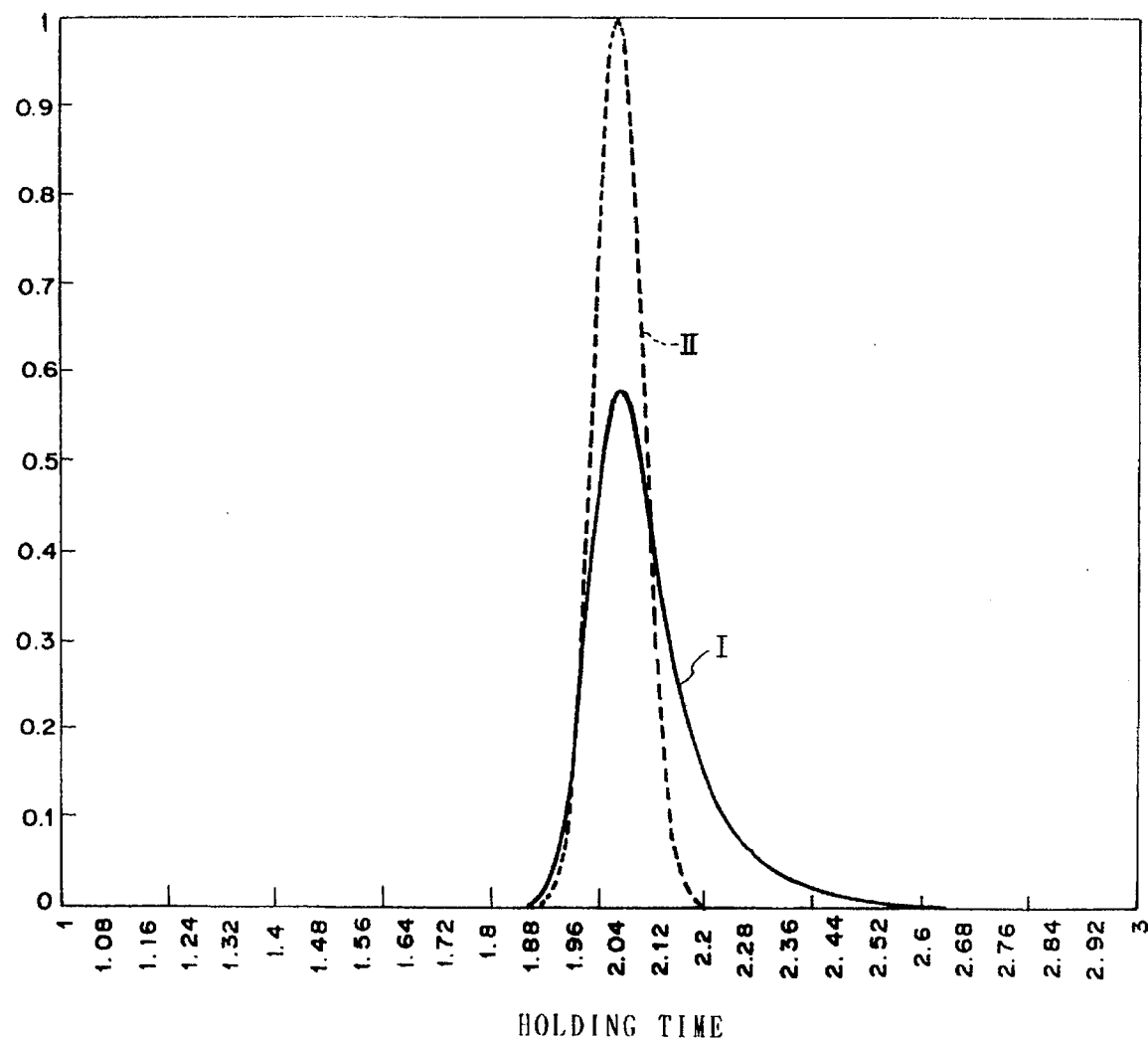
FIG. 17 is a chart comparing the results of detection obtained when the flow cell assembly in accordance with this embodiment of the present invention is used with those obtained when the conventional flow cell assembly is used.

FIG. 17 shows the results of comparison of the case in which the flow cell assembly in accordance with this embodiment is used with the case in which a conventional flow cell assembly having the same shape is used.

As well, in this example of analysis, the same conditions as noted above Table 1 were applied.

In this chart, as compared with curve I indicating the conventional example, curve II indicating this embodiment shows a remarkably high peak with a greatly reduced tailing.

As evidenced above, in the flow cell assembly in accordance with this embodiment of the present invention, even when the clearance 136 of about 0.5 mm exists between the bottom surface 122a of the inlet gasket 122 and the tube 118b, the peak resolution is not adversely affected thereby, while rather greatly reducing tailing.

What is claimed is:

1. A flow cell assembly use for detecting a characteristic of a continuously-flowing fluid, said flow cell comprising a narrow inlet path for said fluid, a flow cell portion having a diameter larger than that of said narrow inlet path, and a flow-regulating portion which is disposed between the narrow inlet path and said flow cell portion, said flow-regulating portion having a diameter substantially the same as that of said flow cell portion and a plurality of flow-regulating holes, said fluid being introduced from said narrow inlet path into said flow cell portion by way of each of the holes of said flow-regulating portion.

2. A flow cell assembly according to claim 1, wherein said flow cell is rectangular and configured so as to satisfy a conditional expression of:

a>3.0 mm wherein a plane perpendicular to a direction of the flow has a size of a×a.

3. A flow cell assembly according to claim 2, wherein said flow cell is cylindrical and configured so as to satisfy a conditional expression of:

a>3.0 mm wherein a plane perpendicular to a direction of the flow has a size of a×a.

4. A flow cell assembly according to claim 1, wherein said narrow inlet path opening and said flow-regulating portion have a clearance of not greater than 2 mm there between.

5. A flow cell assembly according to claim 1 wherein a rectangular flow cell whose outer and inner wall surfaces are formed like those of a hollow square pole is used as said flow cell portion, while said flow-regulating portion has at least four holes at portions corresponding to four corners of said rectangular flow cell.

6. A flow cell assembly according to claim 1, wherein said flow cell is rectangular and wherein said fluid to be tested is introduced from below said rectangular flow cell, while incident light enters said rectangular flow cell from one surface thereof and fluorescence emitted from a surface neighboring the one surface of incidence is detected.

7. A flow cell assembly according to claim 1, wherein said flow cell assembly has a flow-cell holding portion which is attached to a lower opening of said flow cell portion by pressure, while said flow-cell holding portion comprises a first opening formed at a center portion thereof into which said narrow inlet path is detachably inserted and a second opening formed on a side of said first opening facing said flow cell portion into which said flow-regulating portion is fitted, such that said flow-cell portion and said narrow inlet path are exchangeable.

* * * * *